US012622859B2

(12) United States Patent
Lefevre et al.

(10) Patent No.: US 12,622,859 B2
(45) Date of Patent: May 12, 2026

(54) ORGANIC COMPOUNDS

(71) Applicant: GIVAUDAN SA, Vernier (CH)

(72) Inventors: Fabrice Lefevre, Auterive (FR); Daniel Auriol, Roques sur Garonne (FR); Cyrille Jarrin, Muret (FR); Patrick Robe, Lanta (FR); Romain Reynaud, Reims (FR)

(73) Assignee: GIVAUDAN SA, Vernier (CH)

( * ) Notice: Subject to any disclaimer, the term of this patent is extended or adjusted under 35 U.S.C. 154(b) by 289 days.

(21) Appl. No.: 17/669,857

(22) Filed: Feb. 11, 2022

(65) Prior Publication Data

US 2022/0280408 A1     Sep. 8, 2022

Related U.S. Application Data

(63) Continuation of application No. 16/493,861, filed as application No. PCT/EP2018/058408 on Apr. 3, 2018, now Pat. No. 11,278,483.

(30) Foreign Application Priority Data

Apr. 4, 2017     (GB) ..................................... 1705403

(51) Int. Cl.
*A61K 8/60*          (2006.01)
*A61Q 15/00*         (2006.01)
(52) U.S. Cl.
CPC .............. *A61K 8/604* (2013.01); *A61Q 15/00* (2013.01); *A61K 2800/30* (2013.01)
(58) Field of Classification Search
None
See application file for complete search history.

(56) References Cited

U.S. PATENT DOCUMENTS

| | | | | |
|---|---|---|---|---|
| 5,719,129 | A * | 2/1998 | Andary .................. | A61Q 17/04 536/18.1 |
| 8,673,327 | B2 * | 3/2014 | Lemoine ................ | A61Q 15/00 424/401 |
| 2002/0037264 | A1 | 3/2002 | Burry et al. | |
| 2008/0176957 | A1 * | 7/2008 | Joerger .................. | A61K 8/893 514/738 |
| 2016/0331676 | A1 | 11/2016 | Laville et al. | |

FOREIGN PATENT DOCUMENTS

| | | |
|---|---|---|
| CN | 101301297 A | 11/2008 |
| CN | 101411753 A | 4/2009 |
| CN | 104822386 A | 8/2015 |
| EP | 1498131 A1 | 1/2005 |
| JP | H06508601 A | 9/1994 |
| JP | 2002255776 A | 9/2002 |
| JP | 2005187474 A | 7/2005 |
| JP | 2009263279 A | 11/2009 |
| RU | 2396940 C2 | 8/2010 |
| WO | 2006114188 A1 | 11/2006 |

OTHER PUBLICATIONS

Viron, C. et al., Isolation of Phenylpropanoid Glycosides from Orobanche rapum by High Speed Countercurrent Chromatography, Phytochem. Anal. 9 (1998) pp. 39-43. (Year: 1998).*
International Search Report and Written Opinion of the International Searching Authority for corresponding application PCT/EP2018/058408 dated Aug. 13, 2018.
GB Search Report for corresponding application GB 1705403.2 dated Jan. 10, 2018.
G. Marti-Mestres, et al., "The 'in-vitro' percutaneous penetration of three antioxidant compounds", Int. Journal of Pharmaceutics, vol. 331, No. 1, 2007, pp. 139-144.
Renimel, et al., "Nouvel Anti-Radicalaire Naturel:Orbanche Rapum", Rivista Italiana EPPOS: Pubblicazione Tecnico-Scientifica, vol. 9, SPI, 1998, pp. 265-268.
C. Viron et al., "Isolation of Phenylpropanoid Glycosides from Orobanche rapum by High Speed Countercurrant Chromatography", Phytochemical Analysis, vol. 9, No. 1, 1998, pp. 39-43.
XP002781110,"Face and Decollete Velvet Cream SPF 30", Laboratoires Liérac, found on http://www.gnpd.com.
XP002781111, "No Age Essential Serum", Parfums Christian Dior, found on http://www.gnpd.com.
Liqiang, et al.; "New Manual of Active Ingredients of Common Traditional Chinese Medicine", 1st Edition, pp. 159-163, China Union Medical College Press, Jan. 31, 2008, with partial English translation.
Wang Wenshu, et al.; "Chemical Constituents and Pharmacological Efficacies of Medicinal Plants in Ethnic Areas of China", 1st Edition, pp. 233-236, China Minzu University Press, Sep. 30, 2013.
Jiang Jiwu, et al.; "Dictionary of Medicinal Plants", 1st Edition, p. 555, Tianjin Science and Technology Press, Apr. 30, 2005.
Dongchun, et al.; "Pharmacodynamic Effects of the Extracts from Orobanche cumana", Shenyang Pharmaceutical University, 2000, with English abstract.

* cited by examiner

*Primary Examiner* — Dominic Lazaro
(74) *Attorney, Agent, or Firm* — Norris McLaughlin, PA

(57)     ABSTRACT

A cosmetic ingredient comprising crenatoside and acteoside when applied to the skin is useful to provide cosmetic and perfumery benefits.

17 Claims, No Drawings
Specification includes a Sequence Listing.

ORGANIC COMPOUNDS

This is a Continuation application of copending application U.S. Ser. No. 16/493,861, which in turn was an application filed under 35 USC 371 based on PCT/EP2018/058408, filed 3 Apr. 2018, which in turn is based on GB 1705403.2 filed 4 Apr. 2017. The present application claims the full priority benefit of all prior applications and incorporates by reference their full disclosures as if set forth herein.

The applicant herein incorporates by reference the sequence listing provided herewith, as an accompanying filed titled "geneseq_ST25", dated Mar. 24, 2022 9:39 AM, size of 1 KB. No new matter is presented by entry of the foregoing; the sequence listings were present in this application as originally filed and are found herein at page 13.

The present invention is concerned with cosmetic ingredients, which may be applied topically to the skin in order to provide beneficial effects related to perfumery or to the preservation of skin beauty over time. The invention is particularly concerned with said cosmetic ingredients that are able to exert beneficial effects by influencing the composition of the skin microbiota.

In our 20s, our skin renews itself approximately once every 27 days, whereas in our 50s, this same process takes up to 39 days. In other words, in only a matter of a few decades, our skin needs about 44% more time to renew itself.

The skin regeneration process is complex. The process of maintaining skin health and beauty begins with stem cell activation in the basal layer of the skin, upwards through to the superficial layers of the stratum corneum and the stratum microbium.

The stratum microbium is a term that refers to the massive amount of beneficial microorganisms that colonize the surface of our skin, and although it is not technically a layer of skin, it does interact symbiotically with the skin to enable individuals to maintain their health on a daily basis. The stratum microbium remains in a state of flux, in which the composition of the resident microflora (or microbiota) changes over time in response to factors both intrinsic and extrinsic to the host. It is now recognized that a healthy, balanced microbiota can provide not only health benefits, but also cosmetic benefits to the human host.

There is a need to improve the health and/or appearance of human skin by providing cosmetic ingredients as well as methods of cosmetic intervention that can provide beneficial effects, such as accelerating the skin rejuvenation process, and can deliver targeted biological action holistically from the lower to the higher layers of the epidermis, as well as promote a healthy, balanced microbiota.

The applicant has surprisingly discovered a cosmetic ingredient that addresses the deficiencies of the prior art.

Accordingly, the invention provides in a first aspect a cosmetic ingredient comprising a mixture of crenatoside and acteoside.

In another aspect, the invention provides a method of improving the condition or appearance of human skin, the method comprises the step of topically applying to the skin the cosmetic ingredient.

In another aspect, the invention provides a method of balancing the skin microbiota of a human host, the method comprising the step of topically applying to the skin the cosmetic ingredient.

In another aspect, the invention provides a formulation suitable for topical application to the skin containing the cosmetic ingredient.

These and other aspects of the invention will be further understood in view of the following detailed description of particular embodiments of the invention.

The cosmetic ingredient of the present invention may be a plant extract enriched in crenatoside and acteoside.

The plant extract may be obtained from plants of the Orobanchaceae family, and more particularly from Orobanche rapum.

Although the compounds crenatoside and acteoside are both water-soluble, the applicant found that they were unstable in water. Consequently, the extract is preferably obtained by extracting the compounds from plant material using an alcohol, and more particularly ethanol. It is particularly preferred if the alcohol is water-free.

In order to ensure that the extract is stable in terms of both actives' content and colouration, it is desirable that the cosmetic ingredient of the present invention is presented as an extract in a hydric solvent.

A hydric solvent, as the term is used in the present invention, refers to a solvent that contains at least two hydroxyl groups. Suitable hydric solvents include glycerol or glycols, such as dipropylene glycol, diethylene glycol, dibutylene glycol, propylene glycol, butylene glycol, pentylene glycol, heptylene glycol, and hexylene glycol.

A particularly preferred solvent for use in the extract is 1,3-propanediol.

The plant material can be extracted directly using a hydric solvent referred to above. However, it is preferred if an alcohol, such as ethanol, is employed as the extracting medium, and a subsequent solvent-exchange step is carried out to replace the extraction solvent with a hydric solvent in order to stabilize the cosmetic ingredient. The extraction solvent can be removed in a relatively straightforward manner if it is a lower boiling solvent compared to the hydric solvent.

In an embodiment of the present invention, the cosmetic ingredient in the form of a plant extract may be obtained in a process comprising the steps of:

I) Extracting a plant source containing the compounds crenatoside and acteoside in an extraction solvent, preferably ethanol;

II) Filtering the extract to remove solids;

III) Carrying out a solvent-exchange step comprising mixing the extract with a hydric solvent and removing the extraction solvent by evaporation;

IV) Optionally decolourizing the extract obtained in step III), using a suitable decolourizing agent, such as activated charcoal;

V) Filtering the extract to remove solids; and

VI) Optionally adjusting the extract to the desired dry matter content by evaporation.

The cosmetic ingredient of the present invention is characterized by a very high content of crenatoside and acteoside. In an embodiment of the invention, the cosmetic ingredient in the form of a plant extract contains at least 15 wt %, more particularly at least 16 wt %, more particularly at least 17 wt %, more particularly at least 18 wt %, and more particularly at least 19 wt % of a mixture of crenatoside and acteoside, based on the total weight of the dry matter of the extract. In an embodiment, said mixture comprises about 20 wt % to about 60 wt % of crenatoside and about 80 wt % to about 40 wt % of acteoside, based on the total weight of said mixture, preferably about 30 wt % to about 50 wt % of crenatoside and about 70 wt % to about 50 wt % of acteoside, more preferably about 35 wt % to about 45 wt % of crenatoside and about 65 wt % to about 55 wt % of acteoside, for example about 40 wt % of crenatoside and about 60 wt % of acteoside. It is also possible that the cosmetic ingredient of the present invention contains at least 15 wt %, more particularly at least 16 wt %, more particularly at least 17 wt %, more particularly at least 18 wt %, and more particularly at least 19 wt % of each of crenatoside and acteoside, based on the total weight of the dry matter of the extract.

It is an advantage of the present invention that the cosmetic ingredient is easily incorporated into all manner of formulations suitable for use in topical applications, including cosmetic preparations and fine fragrances.

Since highly coloured ingredients may be unacceptable as raw materials for manufacturers of cosmetic preparations or fine fragrances, it is highly advantageous that the cosmetic ingredient according to the invention can be prepared such that its colour or hue will not alter or impair the colour tone of any cosmetic preparation or fine fragrance into which they might be incorporated at levels required to deliver the desired cosmetic or other beneficial effect.

It is a particular advantage of the present invention that cosmetic ingredients in the form of plant extracts can be obtained having a requisite lightness of colour or hue, which enables them to be used at efficacious levels in cosmetic preparations of fine fragrance applications, without affecting the tone of the cosmetic preparation or fine fragrance.

The lightness and hue of the cosmetic ingredient can be characterized by CIELAB chromaticity coordinates L* a* b* according to colorimetric methods known in the art. The L* value is a value specifying the lightness of a substance and is indicated by a value between 0 and 100. An L* value of 100 indicates the brightest state (completely white), and an L* value of 0 indicates the darkest state (completely black). The b* value specifies the blue-yellow hue of a substance. The larger is the b* value, the higher is the degree of yellowness. The smaller is the b* value, the higher is the degree of blueness.

The L* a* b* values of a sample may be measured using any suitable commercially available spectrophotometer, such as a Lico 690. The spectrophotometer is typically powered up for at least one hour before making a measurement. A glass container provided therefor should be half filled with a sample to be measured taking care to ensure that the bottom of the container is fully covered by the sample. Thereafter, the filled container should be placed in the sample stand provided therefor. The sample key on the instrument should be pressed and the L* a* and b* values read off the display panel. Before taking any readings, the instrument should be calibrated for the zero and 100% reflection by placing black and white objects provided therefor on the window of the instruments optical sensor.

In an embodiment of the invention, the cosmetic ingredient has at least one of an L* value of at least about 70; an a* value greater than about 4 and less than about 19; and a b* value greater than about 78 and less than about 91, wherein L*, a* and b* values represent the CIELAB system's chromaticity coordinates.

The cosmetic ingredient according to the present invention can exert a reactivation effect on the natural skin renewal cycle from top to bottom, that is from the superficial layers of the stratum corneum and the stratum microbium to the stem cells in the basal layer of the skin.

In particular, the applicant has demonstrated that the cosmetic ingredient is multi-functional in that it can exert at least one, preferably all, of the following holistic effects on the natural skin renewal cycle:

The cosmetic ingredient of the present invention can provide protection to epidermis stem cells.

The cosmetic ingredient of the present invention can deliver anti-apoptosis activity.

The cosmetic ingredient of the present invention can stimulate epidermis metabolism.

The cosmetic ingredient of the present invention can stimulate epidermis cell differentiation.

The cosmetic ingredient of the present invention can stimulate the production of the skin's barrier components.

The cosmetic ingredient of the present invention can activate the process of natural exfoliation.

The cosmetic ingredient of the present invention can act to maintain the balance of the skin microflora (microbiota).

More particularly, the cosmetic ingredient of the present invention can help stem cells maintain their capability to replicate over time. This effect was demonstrated by observing the clone-forming capacity of stem cells over time when cultivated with and without the cosmetic ingredient using optical microscopy. Still further, in vitro studies examining the effect on human stem cells of daily UV exposure with or without the presence of the cosmetic ingredient demonstrated that levels of the apoptosis inhibiting protein survivin were significantly higher in samples exposed to the cosmetic ingredient.

More particularly, the cosmetic ingredient of the present invention has been shown in studies to inhibit the enzymes Caspase 9 and Caspase 3, both of which are pro-apoptotic enzymes.

More particularly, studies on human skin explants from healthy donors untreated and treated with the cosmetic ingredient of the present invention demonstrate that samples treated with the cosmetic ingredient show increased expression of Ki67 positive cells (measured by immunohistochemistry), which indicates increased cellular metabolism in the epidermis.

More particularly, transcriptomic analysis of epidermis differentiation genes demonstrated stimulation of the expression of certain proteins associated with the epidermis cell differentiation. These proteins included filaggrin, involucrin and loricrin.

More particularly, the cosmetic ingredient of the present invention can increase ceramide production, demonstrating the capability to restore the barrier function of the skin.

More particularly, the cosmetic ingredient of the present invention can stimulate the production of the enzyme Kallikrein 5 protease, which is involved in the desquamation process.

The surface of human skin is home to a wide variety of microorganisms. Collectively, these microorganisms form a microbiome, often referred to as the skin's microbiota. It is generally believed that skin health and appearance requires a balanced collection of skin microorganisms. However, it is known that the balance of the skin's microflora can change over time for intrinsic and extrinsic reasons. For example, certain undesirable microorganisms, such as pathogenic bacteria, molds and yeasts, may attempt to colonize the skin to the detriment of the resident microorganisms; or nutrients that reach the surface of the skin may be effective for some microorganisms, but not others; or sanitizing products that a human host applies to its skin may be relatively more deleterious for some microorganisms than others.

The applicant found, however, that the balance of skin microflora evolved differently over time depending upon whether the skin surface was treated with the cosmetic ingredient of the present invention, or remained untreated. More particularly, the applicant undertook a metagenomic study by swabbing, extracting and sequencing the total microbial DNA of healthy volunteers (women, forearm skin) at a time T=zero and after 14 days, and found that the cosmetic ingredient substantially balanced the compositional make-up of the microbiota, which contained as the main phyla, in terms of relative abundance, Actinobacteria, Cyanobacteria, Proteobacteria, Chloroflexi, Firmicutes, Saccharibacteria, and Bacteroidetes.

By balancing the skin's microbiota favourably in this way, the cosmetic ingredient of the present invention offers beneficial effects for the host, including improvements in skin health and appearance, as well as potentially alleviating a number of skin disorders.

As used herein, the term "balance" as it relates to the microbiota means that the difference in the amount of at least one of the main phyla referred to above on skin treated with the cosmetic ingredient over an appropriate time interval, e.g. 2 weeks, does not change as much (either positively or negatively) as compared to an untreated control. The microbiota is also considered balanced if, during the same time interval, the growth of a pathogen (e.g. Finegoldia magna) is less on skin treated with the cosmetic ingredient as compared to an untreated control.

A method of assessing the balance of the microbiota is set forth in more detail in the examples hereinbelow.

A balanced microbiota can support the health and condition of human skin by means of a number of passive and active mechanisms: Resident microorganisms may passively compete with pathogens for niches on the skin surface or consume nutrients essential for the growth of pathogens. They also actively consume material littering the skin, comprising a mixture of bodily excretions as well as material that is applied to the skin or comes into contact with the skin from external sources, to produce a complex mixture of metabolites and by-products that can inhibit or even kill pathogens.

As a result of the interaction between the microbiota and this cutaneous material, the surface of the skin is home to a mixture of chemical compounds including proteins, lipids, and carbohydrates, as well as metabolites and by-products, which may comprise alcohols, fatty acids, aldehydes, and the like. This complex chemical environment may contain compounds that are volatile and odorous, and which can contribute to the characteristic odour, or malodour, of individuals. Still further, this surface chemistry can influence the manner in which the headspace of a perfume composition applied to the skin will evolve over a period of time.

Perfume ingredients are oils, and the tendency with which they will either rapidly diffuse into the headspace above the skin or partition into the superficial layers of the skin and evaporate slowly will depend to some extent upon the composition of the skin surface chemistry, which is directly influenced by the balance of the microbiota. For example, the hydrophobic/hydrophilic balance of the chemical mixture may cause some perfume ingredients to bloom rapidly into the headspace, and others to become fixed to the surface. Other perfume ingredients may even react with components present on the skin surface.

Controlling the odour emanating from the body is an important cosmetic benefit. Indeed, perfume has been used for centuries as a way to enhance overall personal appearance. In particular, studies have shown that attractiveness could be influenced by smell. It is unclear whether odours alter the visual perception of facial features or, alternatively, how faces are emotionally evaluated by the brain, but what is clear is that pleasant odour and facial attractiveness integrate into one joint emotional evaluation. Furthermore, to the extent that personal well-being can be affected by how attractive an individual feels, or how attractive an individual is perceived to be by others, control of body odour can foster positive social impact within communities as it can change the way that human beings perceive one another.

The use of perfume to mask malodour or to create a pleasant odour emanating from the skin is a benefit that is particularly useful in the context of cosmetic products, because pleasant odours may help to reinforce the impression of health and attractiveness that these products are designed to impart.

In the design of perfumes, such as fine fragrances, a perfume's performance is assessed by the way in which it evaporates from paper blotters. These blotters are cellulosic in nature and provide an evaporation surface that is not representative of the skin. The experienced perfumer will understand that the surface of a blotter is dissimilar to the surface of human skin, and will make allowances for this in perfume design.

But the perfumer's task is complicated if the microbiota is unbalanced and changes unpredictably over time, altering the skin's surface chemistry in a similarly unpredictable way.

Overcoming these technical constraints in order to design perfumes that evaporate more predictably from the surface of the skin is an unmet need.

Surprisingly, the applicant has discovered that using the cosmetic ingredient of the present invention in conjunction with a perfume composition, one is able to balance the skin microbiota over a period of time, and thereby provide a more consistent surface from which a perfume composition can emanate in a more predictable manner.

Still further, by employing the cosmetic ingredient of the present invention to balance the skin's microbiota, the perfumer is able to make a more considered selection of perfume ingredients in order to achieve a particular hedonic effect or to alter the temporal profile of a perfume composition, for example by enhancing the initial bloom of certain perfume ingredients or rendering other perfume ingredients more substantive and long-lasting on the skin's surface.

Accordingly, the invention provides in another of its aspects a method a modulating the evaporation of a perfume composition applied to the surface of the skin, the method comprising the step of applying simultaneously, sequentially or separately the cosmetic ingredient to the skin.

In particular embodiments of the invention, the method of modulating the evaporation of the perfume composition enhances the initial perception of a perfume composition on the skin or enhances retention of a perfume composition on the skin, or both.

Nowadays, many people try to avoid certain commonly employed antiperspirant active ingredients, such as aluminium or zirconium salts or bactericides and bacteriostatic agents, since they are perceived as being unfriendly to human skin, or to populations of micro-flora contained on human skin. Consequently, consumers increasingly wish to transition from antiperspirant to more skin friendly deodorant products. However, they are in some cases dissuaded from doing so because of the possibility of breakthrough malodour in the transition period. Applicant believes that such breakthrough malodour may be the result of changes to the microbiome.

The cosmetic ingredient of the present invention is able to improve the efficacy and long-lastingness of a deodorant composition. In particular, it provides a better malodour reduction and an increased fragrance intensity when used in a deodorant composition (see example 3 below). This is especially advantageous for people changing from an antiperspirant to a deodorant composition, as it reduces the difference between the effects of the two types of composition.

Thus, in another aspect, the present invention provides a method for improving the efficacy and/or long-lastingness of a deodorant composition, comprising the step of adding the cosmetic ingredient to the deodorant composition.

The present invention further relates to a method of facilitating the transition from an antiperspirant to a deodorant composition by providing a deodorant composition comprising the cosmetic ingredient of the present invention. The present invention further relates to the use of the cosmetic ingredient in an antiperspirant or a deodorant composition, and in particular in a deodorant composition comprising no aluminium or zirconium salts.

In another aspect of the invention, there is provided an augmented perfume composition comprising a perfume composition and the cosmetic ingredient defined above.

In a particular embodiment of the invention, the augmented perfume composition is a fine fragrance.

In a more particular embodiment of the invention, the augmented perfume composition is a fine fragrance comprising a perfume composition, the cosmetic ingredient defined above, and ethanol.

The cosmetic ingredient is useful to condition or balance the skin's microflora, and so it is somewhat counter-intuitive to use it in a topical formulation containing large amounts of ethanol, such as a fine fragrance formulation, because one might expect the ethanol to inhibit or kill the microflora. However, in a fine fragrance composition, the cosmetic ingredient of the present invention can help off-set any damage caused to the mircoflora by the ethanol.

As used herein, evaporation of a perfume composition is considered to be modulated if the headspace of the perfume composition above the surface of skin is altered relative to the headspace of the same perfume composition by simultaneous, sequential or separate application of the cosmetic ingredient to the skin surface. By analogy, an augmented perfume composition is a perfume composition that exhibits a modulated headspace by virtue of it containing the cosmetic ingredient defined above.

The discovery that the cosmetic ingredient of the present invention is capable of balancing the skin's microbiota enables the skilled perfumer to create bespoke perfume compositions that contain perfume ingredients selected to evaporate at a pre-defined rate having regard to the compositional make-up of the microbiota and related chemical environment on the skin's surface.

The cosmetic ingredient of the present invention may be applied topically to the skin to provide all manner of beneficial effects, including those related to the preservation of skin beauty over time, as well as the perfume benefits referred to above. In particular, the cosmetic ingredient may be employed in all manner of cosmetic products useful in skin resurfacing; skin renewal activation; skin regeneration; treatment of dry skin; anti-aging; anti-wrinkling; skin moisturizing and hydration; skin barrier reinforcement; natural skin exfoliation; and skin microbiota protection.

Particular cosmetic benefits that can be achieved through the application of the cosmetic ingredient of the present invention include: improving skin appearance, improving skin feel, increasing the thickness of one or more layers of the skin, increasing the elasticity of the skin, increasing the resiliency of the skin, increasing the firmness of the skin, reducing an oily appearance of the skin, reducing a shiny appearance of the skin, reducing a dull appearance of the skin, increasing the hydration of the skin, creating a moisturizing effect on the skin, reducing the appearance of fine lines, reducing the appearance of wrinkles, improving skin texture, improving skin smoothness, improving skin exfoliation, improving skin desquamation, plumping the skin, improving skin barrier properties, improving skin tone, reducing the appearance of redness, reducing the appearance of skin blotches, improving the brightness of the skin, improving the radiance of the skin, and improving the translucence of the skin.

The cosmetic ingredient according to the present invention may be formulated in a formulation suitable for topical application to the skin.

The formulation suitable for topical application may be all manner of personal care products of the leave-on or rinse-off variety, including, but not limited to, make-up preparations, fine fragrances, colognes, toilet water, soaps and detergents, deodorants, douches, feminine hygiene deodorants, shaving preparations, skin care preparations, e.g. cleansing, depilatories, face and neck, body and hand, moisturizers, suntan preparations, e.g. gels, creams, and liquids, and indoor tanning preparations.

The formulation suitable for topical application may contain at least one cosmetically acceptable excipient.

In some embodiments, a cosmetically acceptable excipient refers to a cosmetically acceptable material, composition, or vehicle, such as a liquid or solid filler, diluent, solvent, or encapsulating material. In some embodiments, the excipient is cosmetically acceptable in the sense of being compatible with the other ingredients of a topical formulation, and suitable for use in contact with the skin. Any excipients commonly used in the preparation of formulations suitable for topical application to the human skin, such as cosmetic preparations and fine fragrances, may be employed in the present invention. Suitable excipients include, but are not limited to, ingredients that can influence organoleptic properties, penetration of the skin, and the bioavailability of the cosmetic ingredient. More specifically, they include liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin, and the like.

The formulation for topical application to the skin may take any physical form.

The formulation may be in the form of a liposome composition, mixed liposomes, oleosomes, niosomes, ethosomes, milliparticles, microparticles, nanoparticles and solid-lipid nanoparticles, vesicles, micelles, mixed micelles of surfactants, surfactant-phospholipid mixed micelles, millispheres, microspheres and nanospheres, liposphers, millicapsules, micro-capsules and nanocapsules, as well as microemulsions and nanoemulsions, which can be added to achieve a greater penetration of the cosmetic ingredient.

The formulation may be produced in any solid, liquid, or semi-solid form useful for application to the skin topically. Thus, these preparations of topical application include, but are not restricted to, creams, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, micro-emulsions, emulsions and/or solutions, liquid crystals, anhydrous compositions, aqueous dispersions, oils, milks, balsams, foams, aqueous or oily lotions, aqueous or oily gels, cream, hydro-alcoholic solutions, hydro-glycolic solutions, hydrogels, liniments, sera, soaps, face masks, serums, polysaccharide films, ointments, mousses, pomades, pastes, powders, bars, pencils and sprays or aerosols (sprays), including leave-on and rinse-off formulations.

There now follows a series of examples that serve to further illustrate the invention.

EXAMPLE 1

Preparation of Cosmetic Ingredient

Dried Orobanche rapum, collected manually in Lozére, France, was dried for 1 month in shady conditions before being ground into powder. 1 kg of Orobanche rapum powder was extracted in 6 kg of 96% ethanol in the absence of water. Thereafter, the solid material was separated from the liquid extract by filtration over a cellulosic filter (0.7 micron).

The filtrate was combined with an equal mass of 1,3-propanediol before the ethanol was removed by vacuum evaporation. The resultant extract in 1,3-propanediol was filtered over a charcoal filter. The decolourized extract was adjusted to 1 wt % dry matter and filtered on a 0.3 micron filter.

Analysis by 2D NMR identified two major peaks that representing 18.9 wt % (based on total weight of dry matter), which peaks correspond to crenatoside and acteoside.

EXAMPLE 2

Metagenomic Analysis

Clinical assessments of the cosmetic ingredient formed according to Example 1 were carried out on human volunteers.

A double blind and placebo-controlled clinical evaluation was carried out with 19 women (Age: between 18 and 50 years old, mean age: 39.5 years) having dry skin (corneometer value below 40 AU). All of the subjects participating in the study gave their informed consent signed at the beginning of the study. The measurements were done after 14 and 28 days of use with a test formula (set forth below) containing 0.5% of the extract obtained in accordance with Example 1. A placebo consisted of the same formulation (below) without the extract.

In this study, the evolution of skin metagenome was followed. The body area studied was the forearm.

The test formulation, in the form of a cream, contained the following ingredients:

WATER, CAPRIC/CAPRYLIC TRIGLYCERIDE, CETEARYL WHEAT STRAW GLYCOSIDES, CETEARYL ALCOHOL, EXTRACT OF EXAMPLE 1, PHENOXYETHANOL, DIMETHICONE, METHYL PARABEN, PROPYL PARABEN, ETHYL PARABEN, FRAGRANCE, HEXYL CINNAMAL, BUTYLPHENYL METHYLPROPIONAL, CITRONELLOL, ALPHA ISOMETHYL IONONE, HYDROXYISOHEXYL 3-CYCLOHEXENE CARBOXALDEHYDE, SODIUM HYDROXIDE.

A placebo formulation was identical to the test formulation (above) except that the extract of Example 1 was omitted.

Skin samples of cutaneous microflora were collected from the forearms of healthy volunteers (50 cm$^2$) by a non-invasive swabbing method using sterile swabs moistened with a sterile solution of 0.15 M NaCl. Swabs were transferred at −20° C. and kept frozen until DNA extraction.

DNA extraction was performed using the PowerLyzer® PowerSoil® DNA Isolation Kit (MO BIO Labora-tories, Inc., Carlsbad, USA), with the following modifications. The tip of each swab was detached with a sterile surgical blade and transferred to a 1.5 mL tube to which 750 μL of Bead Solution had been added. The sample biomass was re-suspended by stirring and pipetting and the biological suspension was transferred to a bead beating tube. The remaining steps were performed according to the manufacturer instructions.

Sequencing and DNA analysis was carried out as described below.

16S rRNA gene sequencing:

Sequencing was performed with the MiSeq device (Illumina, Inc., San Diego, CA, USA) through a 500 cycles paired-end run, targeting the V3V4 16S variable regions using the following primers: 16S-Mi341F forward primer 5'-CCTACGGGNGGCWGCAG-3' and 16S-Mi805R reverse primer 5'-GACTACHVGGGTATCTAATCC-3', producing about 460 bp amplicons.

PCR1s were performed as follows: 8 μL of template DNA (0.2 ng) were mixed with 5 μL of each reverse and forward primer (1 μM), 5 μL of KAPA HiFi Fidelity Buffer (5×), 0.8 μL of KAPA dNTP Mix (10 mM each), 0.7 μL of RT-PCR grade water (Ambion), and 0.6 μL of KAPA HiFi hotstart Taq (1 U/μL), for a total volume of 25 μL. Each amplification was duplicated, and duplicates were pooled after amplification. PCR1 cycles consisted of 95° C. for 3 min and then 32 cycles of 95° C. for 30 s, 59° C. for 30 s, and 72° C. for 30 s, followed by a final extension at 72° C. for 3 min, with a BioRad CFX1000 thermocycler. Negative and positive controls were included in all steps to check for contamination. All duplicate pools were controlled by gel electrophoresis, and amplicons were quantified using fluorometry.

Libraries ready for analysis were then produced following the Illumina guidelines for 16S metagenomics libraries preparation. Briefly, the PCR1 amplicons were purified and controlled using an Agilent 2100 Bioanalyzer (Agilent Technologies, Santa Clara, USA). To enable the simultaneous analysis of multiple samples (multiplexing), Nextera® XT indexes (Illumina) were added during PCR2 using between 15 to 30 ng of PCR1 amplicons. PCR2 cycles consisted of 94° C. for 1 min and then 12 cycles of 94° C. for 60 s, 65° C. for 60 s, and 72° C. for 60 s, followed by a final extension at 72° C. for 10 min. Indexed libraries were purified, quantified and controlled using an Agilent 2100 Bioanalyzer. Validated indexed libraries were pooled in order to obtain an equimolar mixture.

The run (500 cycles) was achieved on MiSeq sequencer (Illumina) using the MiSeq Reagent Kit v3 600 cycles (Illumina). The sequencing run produced an output of 25 million of paired-end reads of 250 bases, i.e. up to 6 Gigabases. The libraries and the MiSeq run were performed by Libragen, at the GeT-PlaGe platform (INRA, Auzeville, France).

After MiSeq run, raw data sequences were de-multiplexed and quality-checked to remove all reads with ambiguous bases. Indexes and primer sequences were then trimmed, and the forward and reverse sequences were paired. The paired-sequences were then treated using in-house pipeline to remove chimeras and reads with PCR errors and to split sequences into Operational Taxonomic Unit (OTU) at a 1% dissimilarity level. Good quality binned paired-sequences were mapped to the SILVA SSU Ref database (Release 123; https://www.arb-silva.de/) for taxonomic assignation. Data were then normalized, and compared using White's non-parametric test (White et al., 2009).

The results are shown in the following two tables.

in the relative abundance of *Finegoldia* over the 14 day test period (−58%). On the other hand, when skin is treated with the placebo formulation ("Vehicle"), the level of Finegoldia remains stable. These finding suggest that the cosmetic ingredient inhibits the growth of opportunistic pathogens.

EXAMPLE 3

Deodorant Composition

In order to assess the effect of the cosmetic ingredient of the present invention on deodorant efficacy, a double blind study on 10 volunteers was conducted. All volunteers were antiperspirant users.

TABLE 1

Forearm microbiota phyla composition after 14 days of treatment with Vehicle and Vehicle + Active

| | Vehicle | | | Vehicle + Active | | |
|---|---|---|---|---|---|---|
| Phylum | D 0-Active: mean rel. frequ. (%) | D 14-Active: mean rel. frequ. (%) | p-value | D 0-Active: mean rel. frequ. (%) | D 14-Active: mean rel. frequ. (%) | p-value |
| *Actinobacteria* | 38.71 | 34.42 | 0.387 | 38.05 | 33.88 | 0.443 |
| *Proteobacteria* | 26.78 | 22.27 | 0.372 | 27.25 | 25.73 | 0.775 |
| *Firmicutes* | 26.19 | 37.00 | 0.025 | 26.10 | 29.47 | 0.486 |
| *Bacteroidetes* | 6.18 | 3.61 | 0.144 | 6.62 | 3.94 | 0.176 |
| *Cyanobacteria* | 1.15 | 1.91 | 0.496 | 1.36 | 6.04 | 0.272 |
| *Soccharibacteria* | 0.14 | 0.09 | 0.092 | 0.09 | 0.08 | 0.852 |
| *Chloroflexi* | 0.11 | 0.09 | 0.794 | 0.07 | 0.14 | 0.061 |

Table 1 lists the main phyla (in terms of relative abundance) found in the study. Table 1 also demonstrates that the microbiota evolves differently depending on whether skin was treated with the test formulation ("Vehicle+Active") or the placebo ("Vehicle") formulation. At the phylum level, skin treated with the placebo formulation exhibited a significant increase of Firmicutes between D0 and D14, whereas the levels of other phyla remained substantially stable. On the other hand, for skin treated with the test formulation, levels of all phyla, including Firmicutes, remained substantially stable.

It can be concluded that the cosmetic ingredient stabilises the microbiota and maintains the essential balance of the skin microflora.

The volunteers had to stop using their usual antiperspirant. Instead, they applied a first test deodorant composition on their left underarm and a second test deodorant composition on their right underarm each morning.

At the end of a five-day test period, the volunteers made a self-assessment of the malodour and the fragrance for each side.

Both test deodorant compositions were provided in the form of a spray and contained the following standard deodorant base:

TABLE 2

Comparison of the relative abundances of *Finegoldia magna* at D 0 and D 14

| | Vehicle + Active 0.5% | | | Vehicle | | |
|---|---|---|---|---|---|---|
| Genus | D 0-Active: mean rel. frequ. (%) | D 14-Active: mean rel. frequ. (%) | p-value | D 0-Active: mean rel. frequ. (%) | D 14-Active: mean rel. frequ. (%) | p-value |
| *Finegoldia* | 3.1 | 1.3 | 0.043 | 1.9 | 2.1 | 0.741 |

Table 2 shows the levels of *Finegoldia magna* on skin treated with test formulation and placebo (Vehicle) over a 14-day period.

*Finegoldia magna* is a species that is a normal inhabitant of human skin and is most frequently Gram positive cocci isolated from infected lesions. *F. magna* is implicated in mono- and poly-microbial infections of skin, bone, heart and meninges. A case of toxic shock syndrome caused by *F. magna* has also been reported in the literature.

Results of the study show that skin treated with the test formulation ("Active 0.5%") exhibits a significant reduction

| 1 wt % | Octyl Dodecanol |
|---|---|
| 36 wt % | Ethyl alcohol 96% |
| 2 wt % | Propylene Glycol |
| 1 wt % | Perfume |
| 60 wt % | Propellant (Isobutane, Propane) |

The above ingredients were mixed without the propellant and supplemented with 1.75 wt % of a fragrance composition. For one of the two test deodorant compositions, 0.5 wt % of the cosmetic ingredient of the present invention was added. The mixtures were filled into a spray container and charged with the propellant.

The self-assessment showed that 9 out of the 10 volunteers found that the test deodorant composition containing the cosmetic ingredient of the present invention provided a better malodour reduction and an increased fragrance intensity.

Thus, the cosmetic ingredient of the present invention is able to improve the long-lastingness of a deodorant composition.

4. The cosmetic ingredient of claim 1, wherein the water-free organic extraction solvent is ethanol.

5. The cosmetic ingredient of claim 1, wherein the hydric solvent further comprises a further hydric solvent which comprises at least two hydroxyl groups.

6. The cosmetic ingredient of claim 5, wherein the further hydric solvent is selected from the group consisting of: glycerol, dipropylene glycol, diethylene glycol, dibutylene glycol, propylene glycol, butylene glycol, pentylene glycol, heptylene glycol, and mixtures thereof.

---

---

The invention claimed is:

1. A cosmetic ingredient comprising a plant extract which contains at least 15 wt % of a mixture of crenatoside and acetoside, based on the total weight of the dry matter of the plant extract, wherein the plant extract is obtained by a process comprising the steps:

I) extracting a plant source containing crenatoside and acteoside in a water-free organic extraction solvent;

II) filtering the crude extract to remove solids in order to obtain a filtered extract;

III) carrying out a solvent-exchange step comprising mixing the filtered extract with a hydric solvent, and removing the organic extraction solvent by evaporation in order to obtain an extract, wherein the hydric solvent comprises 1,3-propandiol;

IV) optionally decolorizing the extract obtained in III) with a decolorizing agent;

V) filtering the extract obtained in III) or IV) to remove solids in order to obtain the plant extract; and VI) optionally adjusting the dry matter content of the plant extract in V) by evaporation.

2. The cosmetic ingredient according to claim 1, wherein the mixture comprises about 20 wt % to about 60 wt % of crenatoside and about 80 wt % to about 40 wt % of acteoside, based on the total weight of said mixture.

3. The cosmetic ingredient according to claim 2, wherein the cosmetic ingredient of the present invention contains at least 15 wt % of each of crenatoside and acteoside, based on the total weight of the dry matter of the plant extract.

7. A formulation adapted for topical application to the skin comprising the cosmetic ingredient according to claim 1.

8. The formulation according to claim 7, comprising a perfume composition containing at least one perfume ingredient.

9. The formulation according to claim 7, selected from the group consisting of: a cosmetic cream, cosmetic lotion, cosmetic body spray, cosmetic serum, a deodorant or antiperspirant, or a fine fragrance.

10. A deodorant composition or an antiperspirant composition which comprises the cosmetic ingredient of claim 1, and further wherein the deodorant composition or antiperspirant composition comprises no aluminium salts or zirconium salts.

11. A topical treatment formulation for application to the skin comprising the cosmetic ingredient of claim 1.

12. The topical treatment formulation according to claim 11, comprising a perfume composition containing at least one perfume ingredient.

13. The topical treatment formulation according to claim 11, which is selected from the group consisting of:

a cosmetic cream, cosmetic lotion, cosmetic body spray, cosmetic serum, a deodorant or antiperspirant, and a fine fragrance.

14. A method of modulating the evaporation of a perfume composition applied to the skin, the method comprising the step of: applying simultaneously, sequentially or separately the cosmetic ingredient according to claim 1 to the skin.

15. A method of facilitating the transition from an antiperspirant to a deodorant composition by providing a deodorant composition comprising the cosmetic ingredient according to claim 1.

16. A method of modulating the evaporation of a perfume composition applied to skin, the method comprising the step of applying simultaneously, sequentially or separately the cosmetic ingredient according to claim 1 to the skin.

17. A method of facilitating the transition from an anti-perspirant to a deodorant composition by providing a deodorant composition comprising the cosmetic ingredient according to claim 1.

\* \* \* \* \*

SEQUENCE LISTING

```
<160> NUMBER OF SEQ ID NOS: 2

<210> SEQ ID NO 1
<211> LENGTH: 17
<212> TYPE: DNA
<213> ORGANISM: Orobanche rapum
<220> FEATURE:
<221> NAME/KEY: misc_feature
<222> LOCATION: (9)..(9)
<223> OTHER INFORMATION: n is a, c, g, or t

<400> SEQUENCE: 1
cctacgggng gcwgcag                                                17

<210> SEQ ID NO 2
<211> LENGTH: 21
<212> TYPE: DNA
<213> ORGANISM: Orobanche rapum

<400> SEQUENCE: 2
gactachvgg gtatctaatc c                                           21
```